United States Patent
Govari

(10) Patent No.: US 11,819,265 B2
(45) Date of Patent: Nov. 21, 2023

(54) CAUTIOUS IRREVERSIBLE-ELECTROPORATION (IRE) PROTOCOL FOR AVOIDING BUBBLE GENERATION

(71) Applicant: BIOSENSE WEBSTER (ISRAEL) LTD., Yokneam (IL)

(72) Inventor: Assaf Govari, Haifa (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 785 days.

(21) Appl. No.: 16/940,831

(22) Filed: Jul. 28, 2020

(65) Prior Publication Data

US 2022/0031387 A1 Feb. 3, 2022

(51) Int. Cl.
*A61B 18/12* (2006.01)
*A61B 18/14* (2006.01)
(Continued)

(52) U.S. Cl.
CPC . *A61B 18/1492* (2013.01); *A61B 2017/00115* (2013.01); *A61B 2018/0022* (2013.01); *A61B 2018/00351* (2013.01); *A61B 2018/00375* (2013.01); *A61B 2018/00577* (2013.01); *A61B 2018/00613* (2013.01); *A61B 2018/00714* (2013.01); *A61B 2018/00839* (2013.01); *A61N 1/327* (2013.01)

(58) Field of Classification Search
CPC ...... A61B 18/1492; A61B 2017/00115; A61B 2018/00214; A61B 2018/0022; A61B 2018/00351; A61B 2018/00375; A61B 2018/00577; A61B 2018/00613; A61B 2018/00714; A61B 2018/00839; A61B 2018/00898
See application file for complete search history.

(56) References Cited

U.S. PATENT DOCUMENTS 6,090,617 A * 7/2000 Meserol ............... C12N 13/00
435/173.6
6,135,998 A * 10/2000 Palanker ............ A61B 18/1206
606/45

(Continued)

FOREIGN PATENT DOCUMENTS

CN 111248994 A 6/2020
WO WO2006112870 A1 10/2006

OTHER PUBLICATIONS

European Search Report for corresponding EPA No. 21165816.6 dated Oct. 6, 2021.
(Continued)

*Primary Examiner* — Michael F Peffley
*Assistant Examiner* — Amanda L Zink

(57) ABSTRACT

An irreversible electroporation (IRE) includes setting an initial IRE protocol for applying IRE pulses by electrodes of a catheter placed in contact with tissue in an organ. A notification is issued to a user upon determining that the initial IRE protocol is expected to cause bubbles in blood. In response to the notification, user input is received from the user, that selects between the initial IRE protocol and an alternative protocol that is not expected to cause the bubbles. The IRE pulses are applied according to the initial IRE protocol or the alternative IRE protocol, depending on the user input.

8 Claims, 2 Drawing Sheets

(51) Int. Cl.
    *A61B 17/00*     (2006.01)
    *A61B 18/00*     (2006.01)
    *A61N 1/32*      (2006.01)

(56) References Cited

U.S. PATENT DOCUMENTS

| | | |
|---|---|---|
| 6,352,535 B1 * | 3/2002 | Lewis .............. A61B 17/22022 |
| | | 607/104 |
| 8,048,067 B2 | 11/2011 | Davalos |
| 8,221,411 B2 | 7/2012 | Francischelli |
| 8,456,182 B2 | 6/2013 | Bar-Tal |
| 10,271,893 B2 | 4/2019 | Stewart |
| 10,342,598 B2 | 7/2019 | Long |
| 10,531,914 B2 | 1/2020 | Stewart |
| 2003/0199050 A1 | 10/2003 | Mangano |
| 2004/0236321 A1 * | 11/2004 | Palanker ................... H05H 1/48 |
| | | 606/49 |
| 2011/0106221 A1 | 5/2011 | Neal, II |
| 2012/0221013 A1 * | 8/2012 | Hawkins ............ A61B 17/2202 |
| | | 606/128 |
| 2013/0006228 A1 | 1/2013 | Johnson |
| 2016/0051324 A1 | 2/2016 | Stewart |
| 2016/0066977 A1 | 3/2016 | Neal, II |
| 2018/0221078 A1 * | 8/2018 | Howard ................. A61B 18/14 |
| 2018/0228539 A1 | 8/2018 | Ku |

OTHER PUBLICATIONS

Fesmire, Christopher C. et al., "Irreversible Electroporation is a thermally mediated ablation modality for pulses on the ordre of one microsend", Bioelectrochemistry, vol. 135, May 5, 2020.

* cited by examiner

CAUTIOUS IRREVERSIBLE-ELECTROPORATION (IRE) PROTOCOL FOR AVOIDING BUBBLE GENERATION

FIELD OF THE INVENTION

The present invention relates generally to invasive ablation, and particularly to irreversible electroporation (IRE) of cardiac tissue.

BACKGROUND OF THE INVENTION

Estimation of invasive ablation parameters and controlling the ablation according to the estimation has been previously proposed in the patent literature. For example, U.S. Patent Application Publication No. 2013/0006228 describes devices for localized delivery of energy and methods of using such devices, particularly for therapeutic treatment of biological tissues. The disclosed methods may involve positioning and deploying the energy delivery members in a target site, and delivering energy through the energy delivery members. In an embodiment, radiofrequency (RF) duty cycle and/or pulse duration can be configured to vary responsive to one or more selected parameters, which can include frequency of the treatment signal, power for the treatment signal, or tissue impedance to the treatment signal.

As another example, U.S. Patent Application Publication No. 2016/0066977 describes a medical system for ablating a tissue site with real-time monitoring during an electroporation treatment procedure. A pulse generator generates a pre-treatment test signal having a frequency of at least 1 MHz prior to the treatment procedure and intra-treatment test signals during the treatment procedure. A treatment control module determines impedance values from the pre-treatment test signal and intra-treatment test signals and determines the progress of electroporation and an end point of treatment in real-time based on the determined impedance values while the treatment progresses.

SUMMARY OF THE INVENTION

An embodiment of the present invention that is described hereinafter provides an irreversible electroporation (IRE) process including setting an initial IRE protocol for applying IRE pulses by electrodes of a catheter placed in contact with tissue in an organ. A notification is issued to a user upon determining that the initial IRE protocol is expected to cause bubbles in the blood. In response to the notification, user input is received from the user, that selects between the initial IRE protocol and an alternative protocol that is not expected to cause the bubbles. The IRE pulses are applied according to the initial IRE protocol or the alternative IRE protocol, depending on the user input.

In some embodiments, receiving the user input includes receiving a partitioning of a sequence of the IRE pulses of the initial IRE protocol into a given number of pulse trains with respective given pauses between the pulse trains.

In some embodiments, the initial IRE protocol and the alternative IRE protocol have the same total number of the IRE pulses. In other embodiments, the alternative IRE protocol has a smaller number of the IRE pulses than the initial IRE protocol.

There is additionally provided, in accordance with another embodiment of the present invention, an irreversible electroporation (IRE) system, including a user interface and a processor. The user interface is configured for setting IRE protocols for applying IRE pulses by electrodes of a catheter placed in contact with tissue in an organ. The processor is configured to (i) issue a notification to a user upon determining that an initial IRE protocol is expected to cause bubbles in the blood, (ii) receive via the user interface, in response to the notification, user input that selects between the initial IRE protocol and an alternative protocol that is not expected to cause the bubbles, and (iii) apply the IRE pulses according to the initial IRE protocol or the alternative IRE protocol, depending on the user input.

BRIEF DESCRIPTION OF THE DRAWINGS

The present invention will be more fully understood from the following detailed description of the embodiments thereof, taken together with the drawings in which.

DETAILED DESCRIPTION OF EMBODIMENTS

Overview

Figure 1:
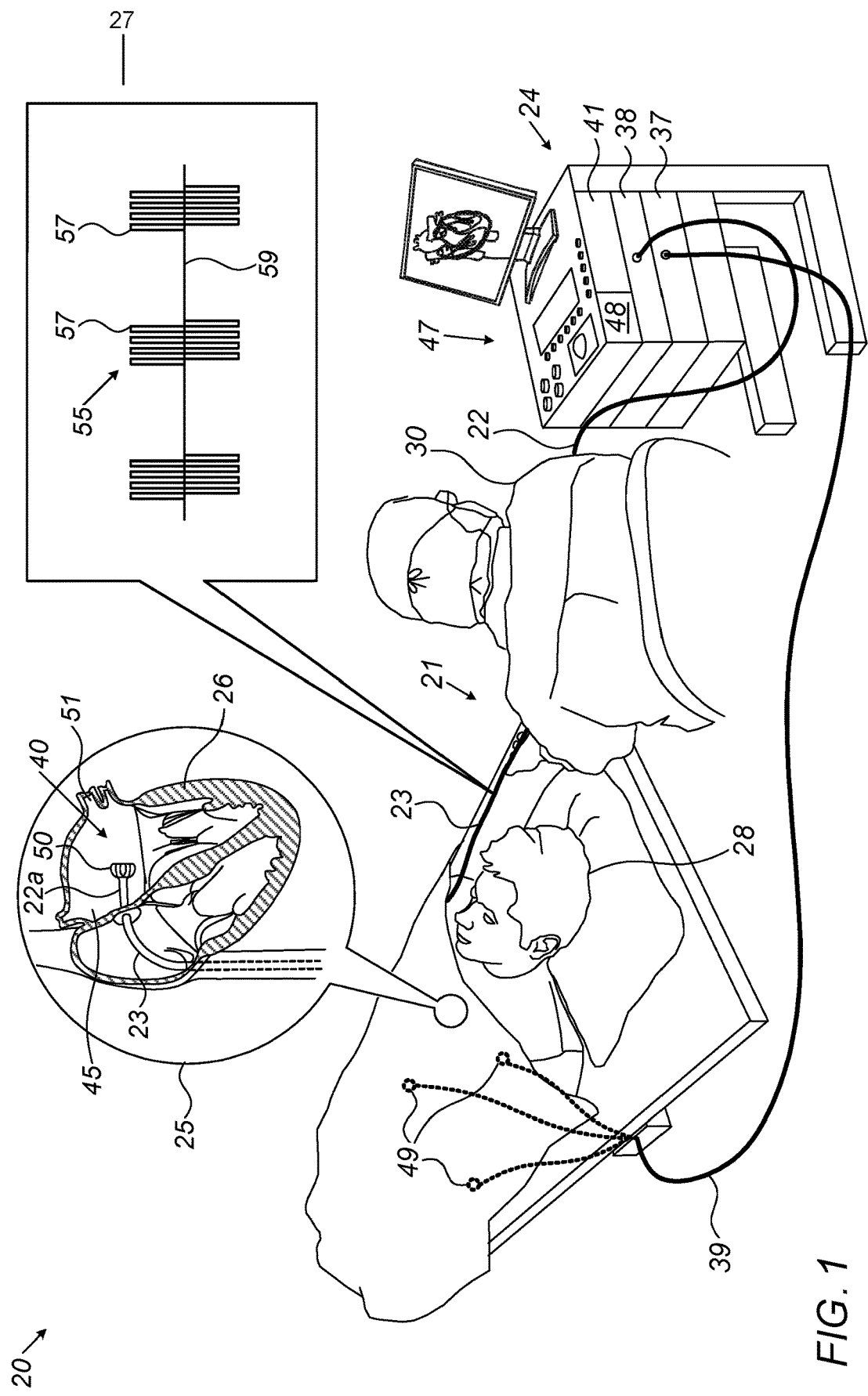
FIG. 1 is a schematic, pictorial illustration of a catheter-based irreversible electroporation (IRE) system, in accordance with an exemplary embodiment of the present invention.

Irreversible electroporation (IRE), also called Pulsed Field Ablation (PFA), may be used as an invasive therapeutic modality to kill tissue cells by subjecting them to high-voltage pulses. Specifically, IRE pulses have a potential use to kill myocardium tissue cells in order to treat cardiac arrhythmia. Cellular destruction occurs when the transmembrane potential exceeds a threshold, leading to cell death and thus the development of a tissue lesion. Therefore, of particular interest is the use of high-voltage bipolar electric pulses (e.g., using a selected pair of electrodes in contact with tissue) to generate high electric fields (e.g., above a certain threshold) to kill tissue cells between the electrodes.

However, the IRE pulses used to ablate tissue may, when the pulses are intense enough, also cause unwanted and/or undesirable effects of potential clinical hazard. For example, a pulse voltage of 1 kV across 100Ω of blood impedance (both possible values) momentarily generates a local peak current of 10 A, i.e., 10 kW in the blood. This voltage, applied between the electrodes to form a sequence of bipolar IRE pulses, may also be high enough to generate enough Joule heating which may, if not quickly dissipated, generate gas bubbles in the blood. Some physicians may elect to accept risk of some bubble formation, although others may prefer not to, typically due to the state of the patient, e.g., a recent stroke.

Embodiments of the present invention that are described hereinafter provide methods and systems for IRE. In some embodiments, various IRE ablation protocols (also called "initial protocols") are evaluated a-priori to determine if they may generate bubbles. The evaluations, performed in the laboratory, may also determine one or more alternative protocols to be proposed to a user. If, during an ablation procedure, the physician (or other user) initially sets an IRE ablation protocol that may generate bubbles, the system notifies the physician, who is then given the choice of using (also called hereinafter, "receiving a user input that selects")

the protocol "as is," or an adapted, more cautious, IRE ablation protocol that does not generate bubbles.

In some embodiments, determining that a selected protocol may generate bubbles means estimating or measuring an impedance between the electrodes in a given electrode-pair and comparing that impedance to a threshold. If the estimated or measured impedance is below the threshold, then the processor determined that dissipated power in blood between the electrode-pair may generate bubbles.

In some embodiments, the more cautious IRE ablation protocol partitions the IRE pulse sequence of the selected protocol into a pulse sequence comprising multiple pulse trains with pauses between them. The pauses permit Joule heating from any pulse to dissipate sufficiently so that bubbles do not form.

In some embodiments, to maintain clinical effect, the more cautious IRE ablation protocol does not change the overall energy dissipated. Rather, the protocol spreads out pulse application time so as to permit more diffusion of generated heat and to lower a maximum temperature caused by the heating. Moreover, the pulse peak voltage is typically not reduced in the cautious IRE ablation protocol, since this affects the electroporation field generated. If the peak voltage is somewhat reduced, it still must be kept above a predefined minimum level required for the IRE ablation to be clinically effective.

In other embodiments, the physician (or other user) can modify, from a user interface, any of the parameters of the cautious protocol, and in particular the number of pulse trains and the minimal pause length. For example, the physician may divide the IRE pulse sequence of the selected protocol into a pulse sequence comprising multiple pulse trains with pauses between them. The pauses permit Joule heating from any pulse to dissipate sufficiently so that bubbles do not form. The user may further decide to lower the total number of pulses, so as to further reduce the accumulative (i.e., overall) electrical power delivered to tissue.

In an embodiment, the system gates the pulse trains to be applied synchronously with the beating of the heart, e.g., to be applied during a refractory period of the tissue. Ventricular and atrial electrograms at ventricular or atrial tissue locations are usually acquired by electrodes in contact with tissue at the location catheter, e.g., during electrophysiological mapping of wall tissue portions of each of the respective cardiac chambers. A ventricular or atrial refractory period is a duration of a pause in neural activity at the tissue location, after an activation occurred there (in tissue of either of the above cardiac chambers). A refractory period typically largely coincides with the QRST interval portion of a cardiac cycle demonstrated in a ventricular or an atrial electrogram taken at the location. A refractory period can be deliberately induced at a tissue portion of the heart, for example, using a pacing catheter to pace the tissue at the tissue location.

Cardiac IRE ablation, in accordance with the disclosed techniques, may be performed using an expandable frame (e.g., balloon or basket) fitted on a distal end of an ablation catheter. In an example procedure, the expandable frame, which is disposed with ablation electrodes, is navigated through the cardiovascular system and inserted into a heart to, for example, ablate an ostium of a pulmonary vein (PV).

By offering a more cautious protocol as an alternative to the initial IRE protocol, IRE ablation procedures, for example in an ostium of a PV using an expandable frame catheter, can be made safer, while maintaining clinical efficacy.

System Description

FIG. 1 is a schematic, pictorial illustration of a catheter-based irreversible electroporation (IRE) system 20, in accordance with an embodiment of the present invention. System 20 comprises a catheter 21, wherein a shaft 22 of the catheter is inserted by a physician 30 through the vascular system of a patient 28 through a sheath 23. The physician 30 then navigates a distal end 22a of shaft 22 to a target location inside a heart 26 of the patient as illustrated in inset 25.

Once distal end 22a of shaft 22 has reached the target location, physician 30 retracts sheath 23 and expands balloon 40, typically by pumping saline into balloon 40. Physician 30 then manipulates shaft 22 such that electrodes 50 disposed on the balloon 40 catheter engage an interior wall of a PV ostium 51 to apply high-voltage IRE pulses via electrodes 50 to ostium 51 tissue.

As seen in insets 25 and 27, distal end 22a is fitted with an expandable balloon 40 comprising multiple equidistant smooth-edge IRE electrodes 50. Due to the flattened shape of the distal portion of balloon 40, the distance between adjacent electrodes 50 remains approximately constant even where electrodes 50 cover the distal portion. Balloon 40 configuration therefore allows more effective (e.g., with approximately uniform electric field strength) electroporation between adjacent electrodes 50 while the smooth edges of electrodes 50 minimize unwanted thermal effects.

Certain aspects of inflatable balloons are addressed, for example, in U.S. Provisional Patent Application No. 62/899,259, filed Sep. 12, 2019, titled "Balloon Catheter with Force Sensor," and in U.S. patent application Ser. No. 16/726,605, filed Dec. 24, 2019, titled, "Contact Force Spring with Mechanical Stops," which are both assigned to the assignee of the present patent application and whose disclosures are incorporated herein by reference.

In the embodiment described herein, catheter 21 may be used for any suitable diagnostic and/or therapeutic purpose, such as electrophysiological sensing and/or the aforementioned IRE isolation of PV ostium 51 tissue in left atrium 45 of heart 26.

The proximal end of catheter 21 is connected to a console 24 comprising an IRE pulse generator 38 configured to apply the IRE pulses between adjacent electrodes 50. The electrodes are connected to IRE pulse generator 38 by electrical wiring running in shaft 22 of catheter 21. A memory 48 of console 24 stores IRE protocols comprising IRE pulse parameters, such as peak bipolar voltage and pulse width.

Console 24 comprises a processor 41, typically a general-purpose computer, with suitable front end and interface circuits 37 for receiving signals from catheter 21 and from external electrodes 49, which are typically placed around the chest of patient 26. For this purpose, processor 41 is connected to external electrodes 49 by wires running through a cable 39.

During a procedure, system 20 can track the respective locations of electrodes 50 inside heart 26, using the Active Current Location (ACL) method, provided by Biosense-Webster (Irvine California), which is described in U.S. Pat. No. 8,456,182, whose disclosure is incorporated herein by reference.

In some embodiments, in case physician 30 is informed by processor 41 of a risk of bubbles using an initially set IRE protocol, physician 30 may select a more cautious protocol that divides (partitions) the IRE pulse delivery 55 of the selected protocol into multiple pulse trains 57 with pauses 59 between the pulse trains as illustrated in inset 27. The pauses permit Joule heating from any pulse to dissipate sufficiently so that bubbles do not form.

In other embodiments, physician 30 can modify, from a user interface 47, any of the parameters of the cautious protocol, and in particular the number of pulse trains and the minimal pause length. For example, the user may decide to remove pulses in a sequence in order to reduce a total number of pulses to be applied. User interface 47 may comprise any suitable type of input device, e.g., a keyboard, a mouse, a trackball and the like.

Processor 41 is typically programmed in software to carry out the functions described herein. The software may be downloaded to the computer in electronic form, over a network, for example, or it may, alternatively or additionally, be provided and/or stored on non-transitory tangible media, such as magnetic, optical, or electronic memory.

In particular, processor 41 runs a dedicated algorithm as disclosed herein, including in FIG. 2, which enables processor 41 to perform the disclosed steps, as further described below. In particular, processor 41 is configured to command IRE pulse generator 38 to output IRE pulses according to a treatment protocol that processor 41 uploads from memory 48.

Cautious Ire Protocol for Avoiding Bubble Generation

Figure 2:
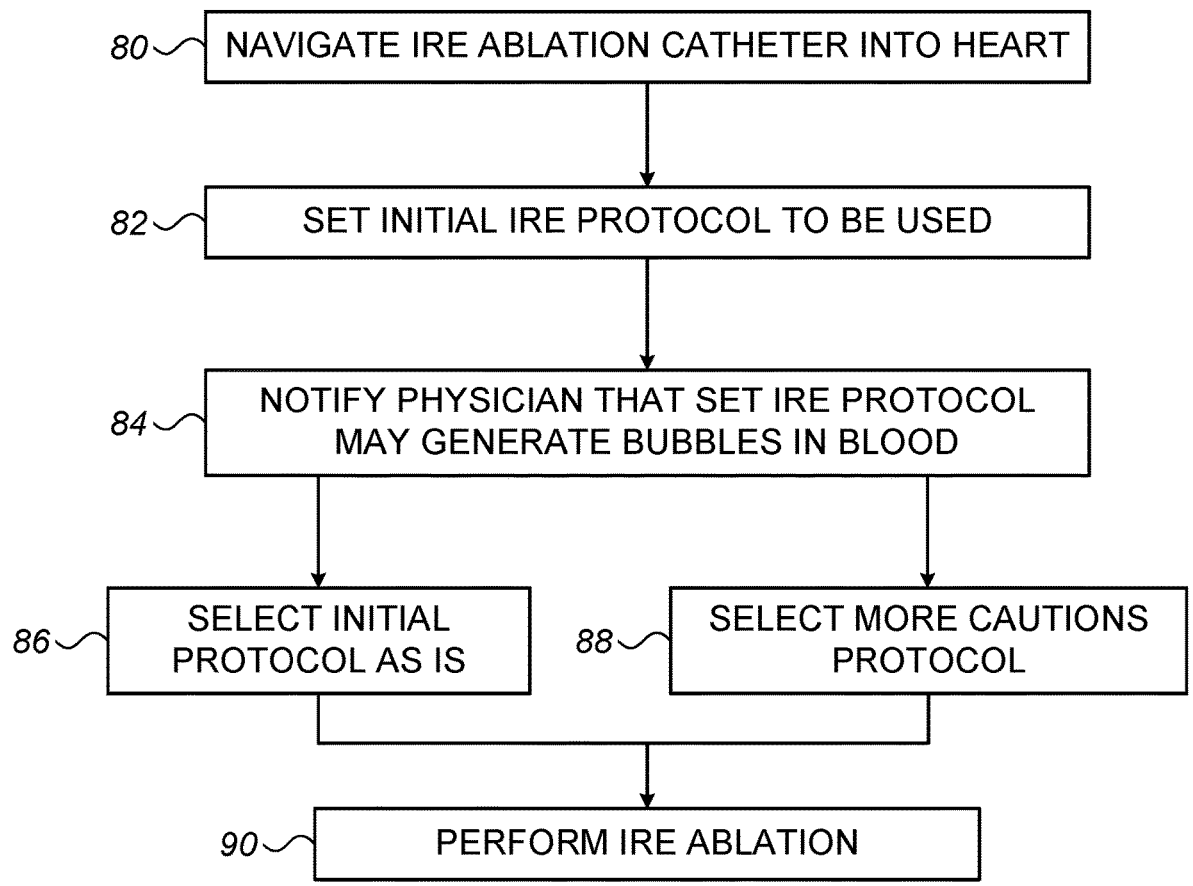
FIG. 2 is a flow chart that schematically illustrates a method for applying irreversible electroporation (IRE) pulses using the system of FIG. 1, in accordance with an exemplary embodiment of the present invention.

FIG. 2 is a flow chart that schematically illustrates a method for applying irreversible electroporation (IRE) pulses using system 20 of FIG. 1, in accordance with an embodiment of the present invention. The algorithm, according to the presented embodiment, carries out a process that begins when physician 30 navigates balloon catheter 40 to a target tissue location in an organ of a patient, such as at PV ostium 51, using, for example, electrode 50 as ACL sensing electrodes, at a balloon catheter navigation step 80.

Next, at an IRE planning step 82, processor 41 uploads a protocol initially set by physician 30, with parameters of the IRE pulses to apply to tissue. An example of IRE ablation settings in an initial protocol that may be used for ablating cardiac tissue using the disclosed balloon 40 is given in Table I.

TABLE I

| Initial Protocol | |
| --- | --- |
| Parameter | Range |
| Preset IRE peak voltage | 1000 V |
| Pulse width | 0.5 mSec |
| Repetition rate | 1 Hz |
| Number of pulses | 40 |

Next, at a notification step 84, processor 41 provides a notification to physician 30 that the initial IRE protocol may generate bubbles in blood. In response, the physician may decide, at a protocol decision step 86, to use the protocol as is (i.e., use the initial protocol). Alternatively, at a protocol replacement decision step 88, the physician decides to change the protocol, for example, into an alternative protocol given in Table II.

TABLE II

| Cautious Protocol | |
| --- | --- |
| Parameter | Range |
| Preset IRE peak voltage | 1000 V |
| Pulse width | 0.5 mSec |
| Repetition rate | 1 Hz |
| Number of pulses | 40 |
| Number of pulse trains | 8 |
| Number of pulses per train | 5 |
| Minimal pause between trains | 2 Sec |

As seen in Table II, in the more cautious protocol the sequence of pulses of Table I is divided into eight pulse trains of five pulses each, with a minimal pause of two seconds between pulse trains.

In an embodiment, physician 30 can modify, from user interface 47, any of the parameters of Table II and, in particular, the number of pulse trains and the minimal pause between pulse trains. Alternatively, the parameters of the alternative protocol may be set automatically by processor 41. In one such embodiment, processor 41 holds a respective alternative protocol for each initial protocol being supported. In another embodiment, processor 41 derives the parameters of the alternative protocol from the parameters of the initial protocol in accordance with some predefined rule or method.

Once an IRE protocol has been chosen (the initial protocol per step 86 or the alternative protocol per step 88), processor 41 commands generator 38 to apply the IRE pulses to tissue, at an IRE treatment step 90. The IRE pulses are applied between selected electrodes of balloon 40 to isolate an arrhythmia originating or propagating via ostium 51.

Although the embodiments described herein mainly address cardiac applications, the methods and systems described herein can also be used in other medical applications, such as in neurology and otolaryngology.

It will thus be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. An irreversible electroporation (IRE) method, comprising:
    setting an initial IRE protocol for applying IRE pulses by electrodes of a catheter placed in contact with tissue in an organ;
    issuing a notification to a user upon determining that the initial IRE protocol is expected to cause bubbles in blood;
    receiving from the user, in response to the notification, user input that selects between the initial IRE protocol and an alternative protocol that is not expected to cause the bubbles; and applying the IRE pulses according to the initial IRE protocol or the alternative IRE protocol, depending on the user input.

2. The method according to claim 1, wherein receiving the user input comprises receiving a partitioning of a sequence of the IRE pulses of the initial IRE protocol into a given number of pulse trains with respective given pauses between the pulse trains.

3. The method according to claim 1, wherein the initial IRE protocol and the alternative IRE protocol have a same total number of the IRE pulses.

4. The method according to claim 1, wherein the alternative IRE protocol has a smaller number of the IRE pulses than the initial IRE protocol.

5. An irreversible electroporation (IRE) system, comprising:
- a user interface configured for setting IRE protocols for applying IRE pulses by electrodes of a catheter placed in contact with tissue in an organ; and
- a processor, which is configured to:
  - issue a notification to a user upon determining that an initial IRE protocol is expected to cause bubbles in blood;
  - receive via the user interface, in response to the notification, user input that selects between the initial IRE protocol and an alternative protocol that is not expected to cause the bubbles; and
  - apply the IRE pulses according to the initial IRE protocol or the alternative IRE protocol, depending on the user input.

6. The system according to claim 5, wherein the processor is configured to receive, in the user input, a partitioning of a sequence of the IRE pulses into a given number of pulse trains with respective given pauses between the pulse trains.

7. The system according to claim 5, wherein the initial IRE protocol and the alternative IRE protocol have a same total number of the IRE pulses.

8. The system according to claim 5, wherein the alternative IRE protocol has a smaller number of pulses than the initial IRE protocol.

* * * * *